US012751778B2

(12) United States Patent
Niikawa et al.

(10) Patent No.: US 12,751,778 B2
(45) Date of Patent: Oct. 6, 2026

(54) CONTINUUM ROBOT SYSTEM

(71) Applicant: CANON KABUSHIKI KAISHA, Tokyo (JP)

(72) Inventors: Yusuke Niikawa, Kanagawa (JP); Tomio Noguchi, Shizuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/769,885

(22) Filed: Jul. 11, 2024

(65) Prior Publication Data

US 2024/0359344 A1 Oct. 31, 2024

Related U.S. Application Data

(63) Continuation of application No. PCT/JP2022/048451, filed on Dec. 28, 2022.

(30) Foreign Application Priority Data

Jan. 14, 2022 (JP) ................................ 2022-004430

(51) Int. Cl.
*A61B 34/30* (2016.01)

(52) U.S. Cl.
CPC ........ *A61B 34/30* (2016.02); *A61B 2034/301* (2016.02); *A61B 2034/303* (2016.02)

(58) Field of Classification Search
CPC ........ A61B 2034/301; A61B 2034/303; A61B 34/32; A61B 34/70
See application file for complete search history.

(56) References Cited

U.S. PATENT DOCUMENTS

| | | | | |
|---|---|---|---|---|
| 6,246,200 | B1 * | 6/2001 | Blumenkranz | A61B 34/70 318/568.25 |
| 7,935,130 | B2 * | 5/2011 | Williams | A61B 34/71 606/208 |
| 7,947,051 | B2 * | 5/2011 | Lee | A61B 34/30 600/407 |
| 8,562,594 | B2 * | 10/2013 | Cooper | A61B 34/30 901/41 |
| 10,299,883 | B2 * | 5/2019 | Kilroy | A61B 90/10 |
| 10,800,030 | B1 * | 10/2020 | Cui | B62B 3/008 |
| 10,813,704 | B2 * | 10/2020 | Kostrzewski | A61B 17/1615 |
| 10,993,760 | B2 * | 5/2021 | Swayze | A61B 34/70 |

(Continued)

FOREIGN PATENT DOCUMENTS

| | | | |
|---|---|---|---|
| CN | 110711032 | A | 1/2020 |
| JP | 2013-505106 | A | 2/2013 |

(Continued)

*Primary Examiner* — Bobby Rushing, Jr.
(74) *Attorney, Agent, or Firm* — Canon U.S.A., Inc., IP Division

(57) ABSTRACT

The present invention is a continuum robot system including a continuum robot including a bendable body and a base portion at which the bendable body is provided; a support base including a moving stage that supports the continuum robot such that the continuum robot is detachable from and attachable to the moving stage and is movable along a straight line; and an arm that supports the support base and that is turnable about a first shaft. The continuum robot moves along a plane perpendicular to the first shaft when the moving stage with the continuum robot mounted on the moving stage is moved.

15 Claims, 8 Drawing Sheets

(56) References Cited

U.S. PATENT DOCUMENTS

| | | | | |
|---|---|---|---|---|
| 11,045,944 | B2 * | 6/2021 | Phipps | G01B 21/045 |
| 2013/0244820 | A1 * | 9/2013 | Solomon | B25J 18/00<br>474/58 |
| 2021/0259794 | A1 | 8/2021 | Kato | |
| 2021/0369366 | A1 | 12/2021 | Hwang et al. | |

FOREIGN PATENT DOCUMENTS

| | | | |
|---|---|---|---|
| JP | 2016514492 | A | 5/2016 |
| JP | 2019155116 | A | 9/2019 |
| JP | 2021100655 | A | 7/2021 |
| JP | 2021137566 | A | 9/2021 |

* cited by examiner

CONTINUUM ROBOT SYSTEM

CROSS-REFERENCE TO RELATED APPLICATIONS

This application is a Continuation of International Patent Application No. PCT/JP2022/048451, filed Dec. 28, 2022, which claims the benefit of Japanese Patent Application No. 2022-004430, filed Jan. 14, 2022, both of which are hereby incorporated by reference herein in their entirety.

TECHNICAL FIELD

The present invention relates to a continuum robot system.

BACKGROUND ART

A medical apparatus constituted by a continuum robot is known. When a bendable medical instrument of the medical apparatus in PTL 1 is to be caused to pass through a relatively wide lumen of a patient, a user manually inserts the bendable medical instrument into the lumen of the patient while the bendable medical instrument is held by the hand of the user. Next, when the bendable medical instrument reaches a first portion, the user attaches the bendable medical instrument to the insertion unit and can continue an insertion step by switching to robot control.

If the user can manually insert the bendable medical instrument into the lumen of the patient in a state in which the bendable medical instrument is attached to the insertion unit, the user is not required to perform the operation of attaching of the bendable medical instrument. Operability of the bendable medical instrument is thus favorably improved.

The manual insertion in a state in which the bendable medical instrument is attached to the insertion unit may be difficult.

An object of the present invention is to improve operability of a continuum robot.

CITATION LIST

Patent Literature

PTL 1: U.S. Unexamined Patent Application Publication No. 2021/259794

SUMMARY OF INVENTION

The present invention is a continuum robot system including a continuum robot that includes a bendable body and a base portion at which the bendable body is provided; a support base that includes a moving stage that supports the continuum robot such that the continuum robot is detachable from and attachable to the moving stage and is movable along a straight line; and an arm that supports the support base and that is turnable about a first shaft, in which, when the moving stage is moved with the continuum robot mounted on the moving stage, the continuum robot moves along a plane perpendicular to the first shaft.

Further features of the present invention will become apparent from the following description of exemplary embodiments with reference to the attached drawings.

DESCRIPTION OF EMBODIMENTS

Hereinafter, examples of the present invention will be described with reference to the drawings. Note that dimensions, materials, shapes, arrangement, and the like of components described in the examples should be changed, as appropriate, in accordance with the configuration, various conditions, and the like of an apparatus to which the present invention is applied.

Example 1

Figure 1:
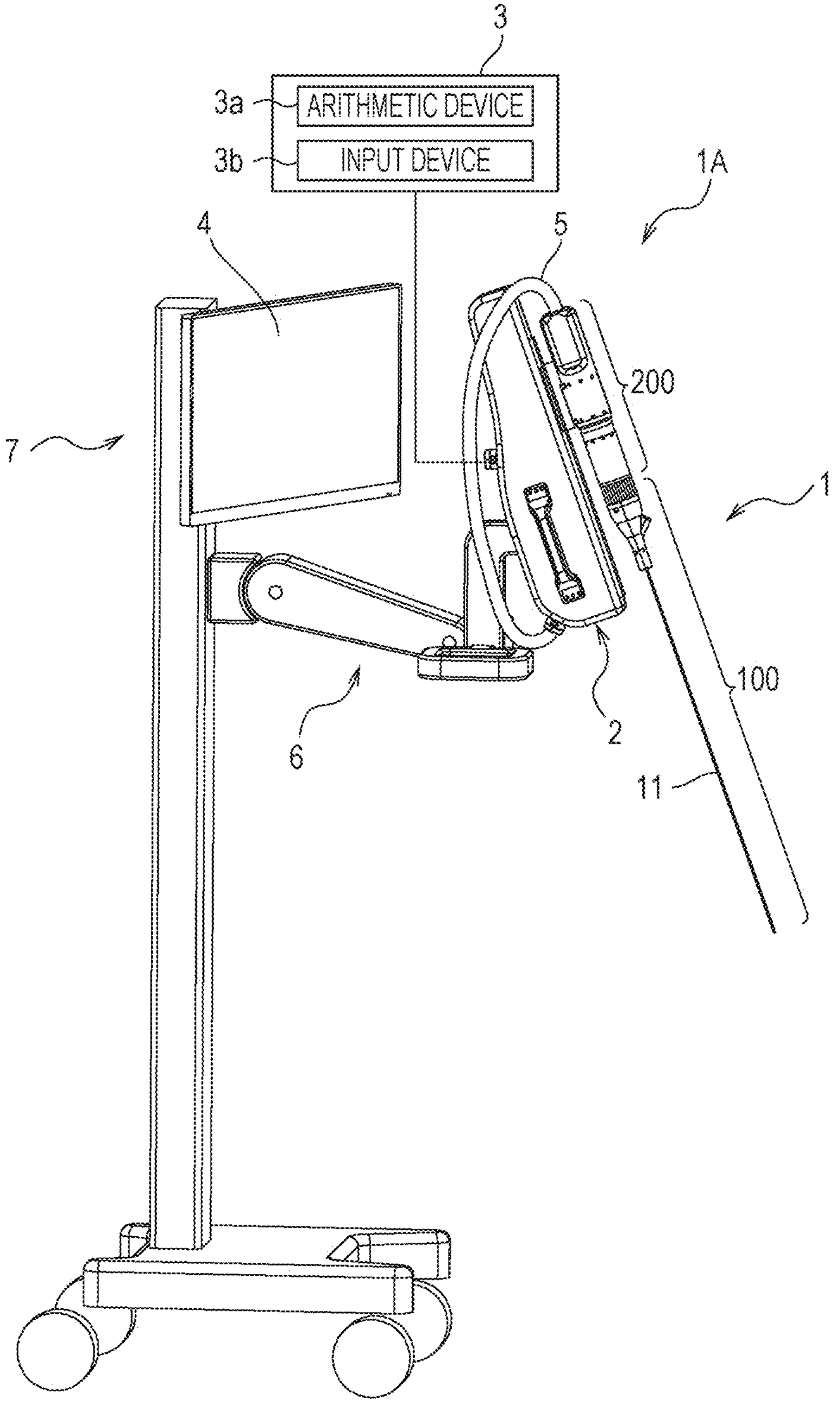
FIG. 1 is a general view of a medical system according to Example 1.
Figure 2:
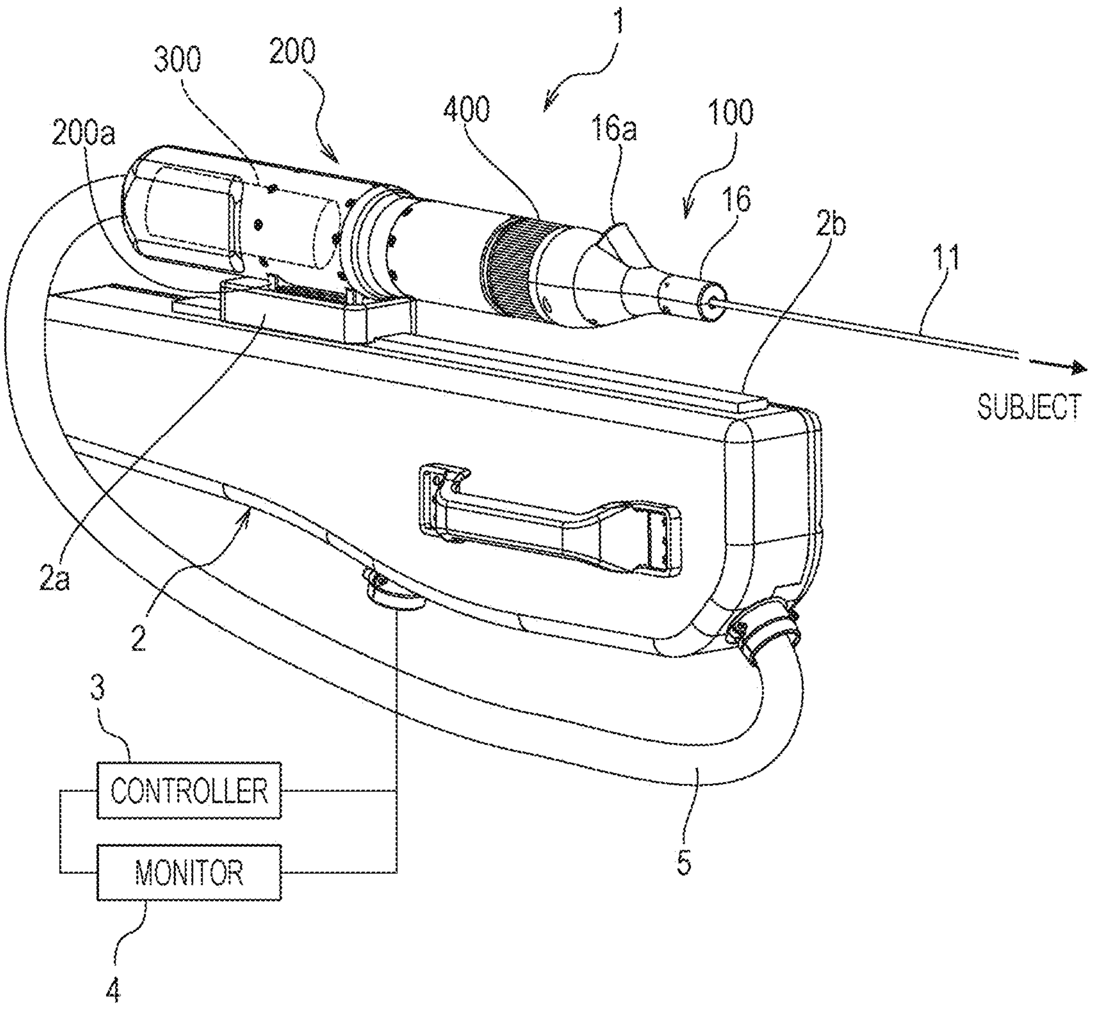
FIG. 2 is a perspective view of a medical apparatus and a support base according to Example 1.

With reference to FIG. 1 and FIG. 2, a medical system 1A according to the present example will be described. FIG. 1 is a general view of the medical system 1A. FIG. 2 is a perspective view of a medical apparatus 1 and a support base 2.

The medical system 1A includes the medical apparatus 1 constituted by a continuum robot, the support base 2 that supports the medical apparatus 1, and an arm 6 that supports the support base 2. The medical system 1A is a continuum robot system to which the present invention is applied. The medical system 1A also includes a controller 3 that controls the medical apparatus 1 and the support base 2; a monitor 4 as a display device; and a cart 7 that supports the monitor 4 and the arm 6 to be movable.

The medical apparatus 1 includes a catheter unit (a bendable unit) 100 that includes a catheter 11 as a bendable body and a base unit (a drive unit, an attachment-target unit) 200 serving as a base portion. The catheter unit 100 is configured to be attachable to and detachable from the base unit 200.

In the present example, a user of the medical system 1A and the medical apparatus 1 can perform work of observation of the inside of a subject, collection of various specimens from the inside of the subject, treatment with respect to the inside of the subject, and the like by inserting the catheter 11 into the inside of the subject. In one embodiment, the user can insert the catheter 11 into the inside of a patient as the subject. Specifically, it is possible to perform work of observation, collection, resection, and the like of a lung tissue by inserting the catheter 11 into a bronchial tube through an oral cavity or a nasal cavity of the patient.

The catheter 11 is usable as a guide (sheath) that guides a medical instrument for performing the aforementioned work. Examples of the medical instrument (tool) are an endoscope, forceps, an ablation device, and the like. The catheter 11 itself may have a function as the aforementioned medical instrument.

In the present example, the controller 3 includes an arithmetic device 3*a* and an input device 3*b*. The input device 3*b* receives a command and an input for operating the catheter 11. The arithmetic device 3*a* includes a storage in which a program and various data for controlling the catheter 11 are stored, a random-access memory, and a central processing unit for executing the program. The controller 3 may include an output unit that outputs a signal for displaying an image on the monitor 4.

As illustrated in FIG. 2, the medical apparatus 1 in the present example is electrically connected to the controller 3 through a cable 5 that couples the base unit 200 of the medical apparatus 1 to the support base 2. The medical apparatus 1 and the controller 3 may be directly connected to each other through a cable. The medical apparatus 1 and the controller 3 may be connected to each other wirelessly.

The support base 2 includes a moving stage (receiver) 2*a* and a guide portion 2*b* that supports the moving stage 2*a* to be movable linearly. The moving stage 2*a* moves along the guide portion 2*b* by being driven by a motor, which is not illustrated, connected to the controller 3.

The medical apparatus 1 is detachably mounted on the support base 2 with the base unit 200 interposed therebetween. More specifically, an attachment portion (connection portion) 200*a* of the base unit 200 of the medical apparatus 1 is detachably mounted on the moving stage 2*a* of the support base 2. Connection between the medical apparatus 1 and the controller 3 is maintained, even in a state in which the attachment portion 200*a* of the medical apparatus 1 is detached from the moving stage 2*a*, to enable the controller 3 to control the medical apparatus 1. In the present example, the medical apparatus 1 and the support base 2 are connected to each other by the cable 5, even in the state in which the attachment portion 200*a* of the medical apparatus 1 is detached from the moving stage 2*a*.

The medical apparatus 1 moves in response to the moving stage 2*a* moving in a state in which the medical apparatus 1 is attached to the moving stage 2*a*. Then, an operation of moving the catheter 11 in a direction of insertion into a subject and an operation of moving the catheter 11 in a direction of extraction from the subject are performed. Movement of the moving stage 2*a* is controlled by the controller 3.

The attachment portion 200*a* of the base unit 200 includes a detachment switch, which is not illustrated. When the detachment switch is pressed in a state in which the attachment portion 200*a* is mounted on the moving stage 2*a*, the user can detach the medical apparatus 1 from the moving stage 2*a*. In a state in which the attachment portion 200*a* is mounted on the moving stage 2*a* and the detachment switch is not pressed, the medical apparatus 1 is fixed to the moving stage 2*a*.

The medical apparatus 1 includes a wire driver 300 for driving the catheter 11. In the present example, the medical apparatus 1 is a robot catheter apparatus that drives the catheter 11 by the wire driver 300 controlled by the controller 3.

The controller 3 controls the wire driver 300 and can perform an operation of bending the catheter 11. In the present example, the wire driver 300 is incorporated in the base unit 200.

In the extension direction of the catheter 11, an end portion at which the leading end of the catheter 11 that is to be inserted into a subject is disposed is referred to as the distal end. In the extension direction of the catheter 11, a side opposite to the distal end is referred to as the proximal end.

The catheter unit 100 includes a proximal end cover 16 that covers the proximal end side of the catheter 11. The proximal end cover 16 has a tool hole 16*a*. A medical instrument is insertable into the catheter 11 through the tool hole 16*a*.

As described above, the catheter 11 in the present example has a function as a guide device for guiding a medical instrument to a desired position in the inside of a subject.

For example, the catheter 11 is inserted to a target position in the inside of a subject in a state in which an endoscope is inserted into the catheter 11. After the catheter 11 reaches the target position, the endoscope is extracted from the catheter 11 through the tool hole 16*a*. Then, a medical instrument is inserted through the tool hole 16*a*, and work of collection of various specimens from the inside of the subject, treatment with respect to the inside of the subject, and the like are performed.

As described later, the catheter unit 100 is detachably mounted on the base unit 200. The user detaches the catheter unit 100 from the base unit 200 after using the medical apparatus 1 and can use the medical apparatus 1 again by attaching a new catheter unit 100 to the base unit 200.

The medical apparatus 1 includes an operation portion 400. In the present example, the operation portion 400 is included in the catheter unit 100. The operation portion 400 is operated by the user to fix the catheter unit 100 to the base unit 200 and to detach the catheter unit 100 from the base unit 200.

By connecting an endoscope to be inserted into the catheter 11 to the monitor 4, it is possible to cause the monitor 4 to display an image imaged by the endoscope. By connecting the monitor 4 to the controller 3, it is possible to cause the monitor 4 to display a state of the medical apparatus 1 and information relating to control of the medical apparatus 1. For example, the monitor 4 can display the position of the catheter 11 in the inside of the subject and information relating to navigation of the catheter 11 in the inside of the subject. The monitor 4 may be connected to each of the controller 3 and the endoscope by a wire or wirelessly. The monitor 4 and the controller 3 may be connected to each other with the support base 2 interposed therebetween.

Figure 3A:
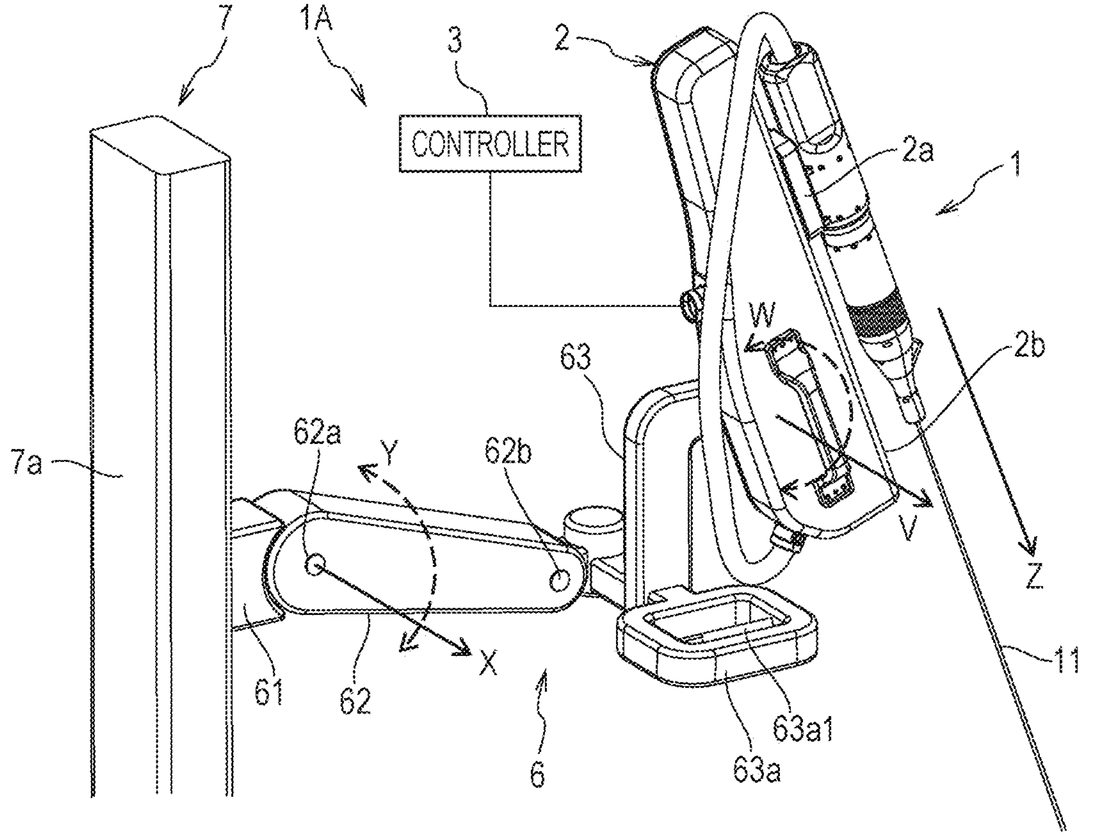
FIG. 3A is a schematic view of the medical system according to Example 1.
Figure 3B:
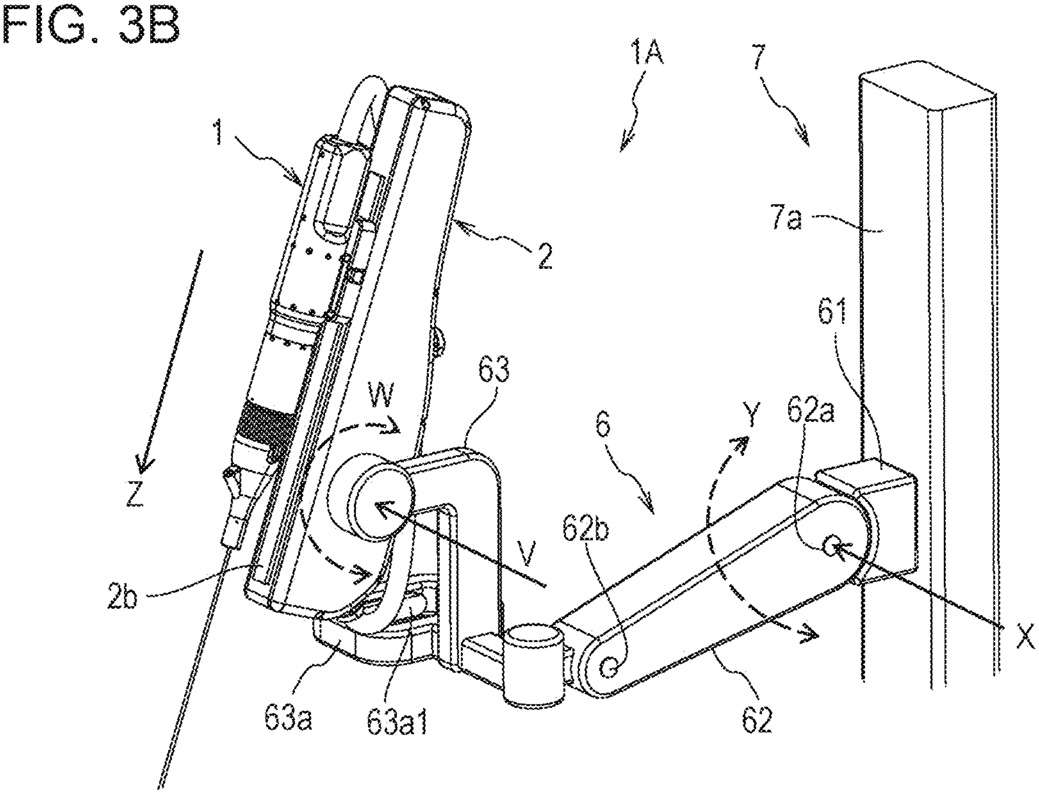
FIG. 3B is a schematic view of the medical system according to Example 1.
Figure 4A:
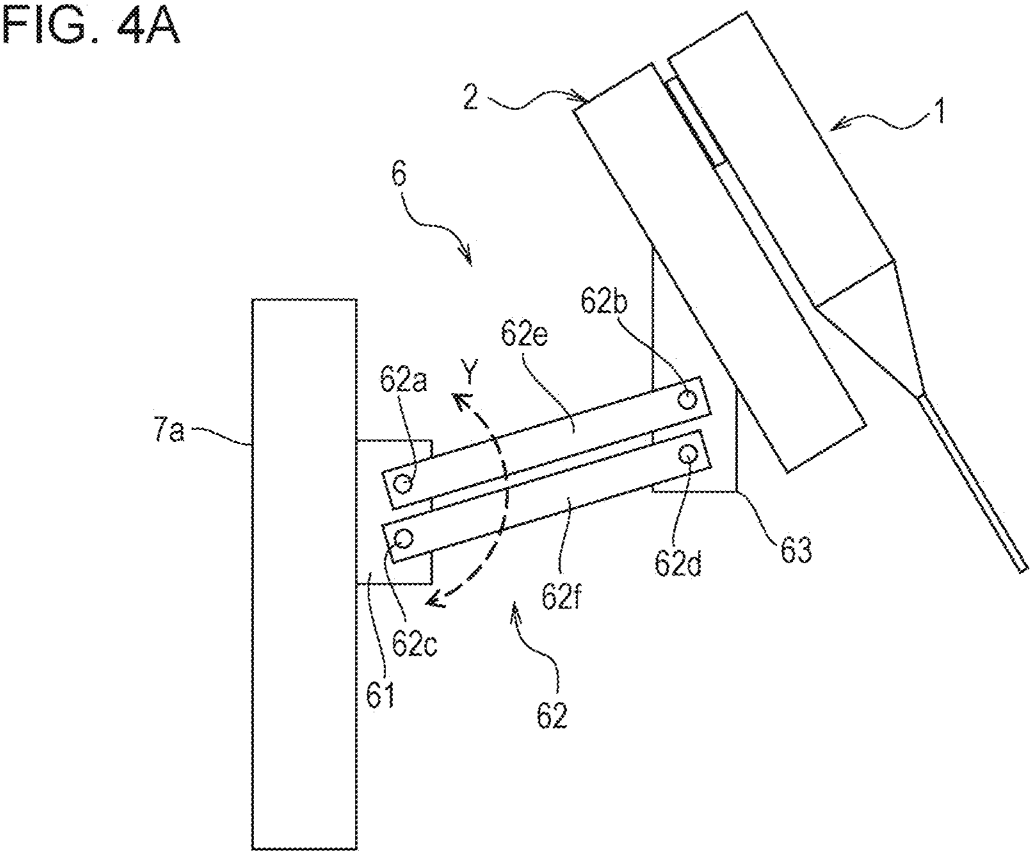
FIG. 4A is a diagram illustrating an internal structure of an arm according to Example 1.
Figure 4B:
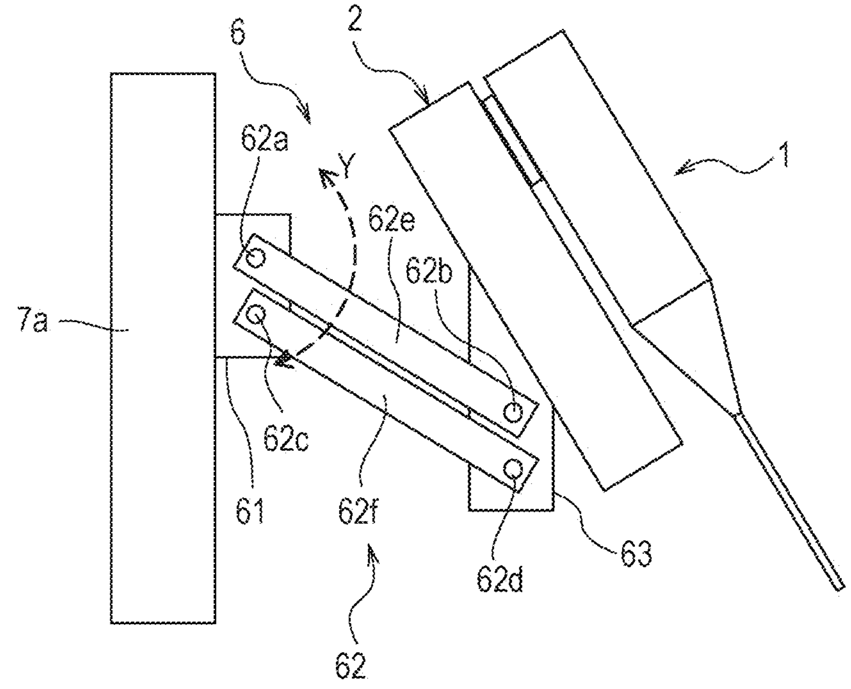
FIG. 4B is a diagram illustrating an internal structure of the arm according to Example 1.

With reference to FIG. 3A, FIG. 3B, FIG. 4A, and FIG. 4B, the arm 6 that supports the support base 2 will be described. FIG. 3A and FIG. 3B are each a schematic view of the medical system 1A according to Example 1. FIG. 3A and FIG. 3B are views from different angles. FIG. 4A and FIG. 4B are each a schematic view for describing an internal structure of the arm 6 according to Example 1.

As illustrated in FIG. 3A and FIG. 3B, the arm 6 is constituted by a base portion 61, a turning portion 62, and a supporting portion 63. The base portion 61 is fixed to a support 7*a* of the cart 7. A first joint shaft 62*a*, which is a first shaft, is disposed at a connecting portion between the base portion 61 and the turning portion 62. The turning portion 62 is supported to be turnable about the first joint shaft 62*a* (axis X) with respect to the base portion 61. A second joint shaft 62*b*, which is a second shaft, is disposed at a connecting portion between the turning portion 62 and the supporting portion 63. The supporting portion 63 is supported to be turnable about the second joint shaft 62*b* with respect to the turning portion 62. The supporting portion 63 supports the support base 2.

Next, an internal structure of the arm 6 will be described with reference to FIG. 4A. The first joint shaft 62*a* and a third joint shaft 62*c* are provided at the base portion 61 of the arm 6. Meanwhile, the second joint shaft 62*b* and a fourth joint shaft 62*d* are provided at the supporting portion 63. A first link arm 62*e* connects the first joint shaft 62*a* and the second joint shaft 62*b* to each other and is turnable about each of the shafts. A second link arm 62*f* connects the third joint shaft 62*c* and the fourth joint shaft 62*d* to each other and is turnable about each of the shafts. The turning portion 62 of the arm 6 thus constitutes a four-joint link. A distance between the first joint shaft 62*a* and the third joint shaft 62*c* and a distance between the second joint shaft 62*b* and the fourth joint shaft 62*d* are substantially identical to each other. A distance (in other words, the length of the first link arm 62*e*) between the first joint shaft 62*a* and the second joint shaft 62*b* and a distance (in other words, the length of the second link arm 62*f*) between the third joint shaft 62*c* and the fourth joint shaft 62*d* are identical to each other. The joint shafts of this four-joint link thus have a relationship of a parallelogram, and the turning portion 62 of the arm 6 constitutes a parallel crank mechanism. Therefore, even when the turning portion 62 of the arm 6 is turned around the first joint shaft 62*a*, the orientation of the support base 2 is kept constant. For example, the orientation of the support base 2 is maintained substantially constant even when the turning portion 62 of the arm 6 in the state illustrated in FIG. 4A is turned around the first joint shaft 62*a* to be moved into the state illustrated in FIG. 4B. The turning direction of the turning portion 62 is indicated by Y in FIG. 4A and FIG. 4B. With the orientation of the support base 2 being maintained substantially constant, the orientation of the medical apparatus 1 supported by the support base 2 is similarly maintained substantially constant.

Here, as illustrated in FIG. 3A and FIG. 3B, the supporting portion 63 of the arm 6 is provided with a handle 63*a* for performing a turning operation of the arm 6. The arm 6 is provided with a lock mechanism as a lock portion, which is not illustrated, that locks the turning operation, and the turning operation is unlocked only while an unlocking button 63*a*1 provided at the handle 63*a* is pressed. Consequently, the turning portion 62 of the arm 6 and the supporting portion 63 are fixed to each other when the handle 63*a* is not operated, and the arm 6 can be prevented from unintentionally moving.

The support base 2 is supported to be turnable by a joint shaft (axis V), which is not illustrated, provided at the supporting portion 63. The axis X and the axis V have a relationship of being parallel to each other. In FIG. 3A and FIG. 3B, the turning direction of the support base 2 at the axis V is indicated by W. The user can freely adjust the orientation of the support base 2 and the orientation of the medical apparatus 1 supported by the support base 2 by turning the support base 2 in the W direction.

A gas spring, which is not illustrated, is provided at the turning portion 62 of the arm 6, and the weights of the medical apparatus 1, the support base 2, and the arm 6 itself can be adjusted to be cancelled. The user thus can perform the turning operation of the arm 6 with a light force.

The support base 2 supported by the supporting portion 63 supports the moving stage 2*a* on which the medical apparatus 1 is mounted such that the moving stage 2*a* is movable along a straight line by being guided by the guide portion 2*b*. The support base 2 is fixed to the supporting portion 63 such that a moving direction Z of the medical apparatus 1 moved by the moving stage 2*a* is perpendicular to the first joint shaft 62*a* (axis X) of the arm 6.

As described above, the user inserts the catheter 11 into the inside of a patient as the subject. Specifically, the catheter 11 is inserted into a bronchial tube through an oral cavity or a nasal cavity of the patient to thereby enable work of observation, collection, resection, and the like of a lung tissue to be performed. Two methods are prepared as measures of inserting the catheter 11 into the inside of a patient.

A first method is a method in which the support base 2 supported by the arm 6 and the medical apparatus 1 are integrally moved by the user by manually moving the turning portion 62 of the arm 6 in a Y-direction. Hereinafter, this method is referred to as manual insertion.

A second method is a method in which the moving stage 2*a* on which the medical apparatus 1 is mounted is linearly moved along the guide portion 2*b* in a Z-direction. Moving by the moving stage 2*a* is driven, in response to an instruction from the user, by a motor, which is not illustrated, connected to the controller 3. Hereinafter, this method is referred to as robot insertion.

Insertion of the catheter 11 in accordance with a required situation can be flexibly applied by switching between the two insertion methods of the manual insertion and the robot insertion. For example, when the catheter 11 is to be first inserted through a large or wide portion of the biological structure of a patient, rapid advancing of the catheter 11 can be accelerated by the manual insertion and can save time as a result. When the catheter 11 reaches a more curvy portion of the biological structure of the patient, insertion of the catheter 11 is switched to the robot insertion. Consequently, the catheter 11 can be inserted more locally. The catheter 11 is inserted slowly at a reduced speed to minimize abrasion and unpleasantness with respect to the patient.

Figure 5A:
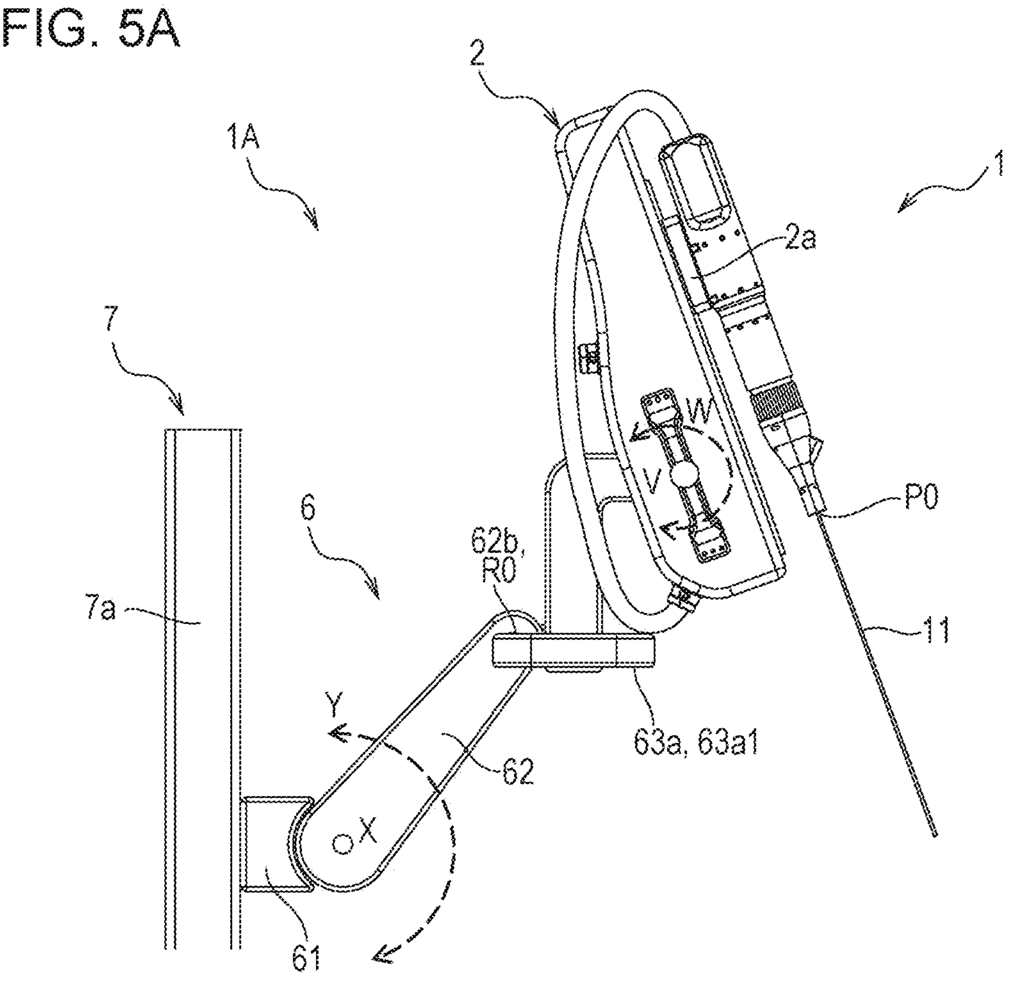
FIG. 5A is a schematic view of the medical system according to Example 1.
Figure 5B:
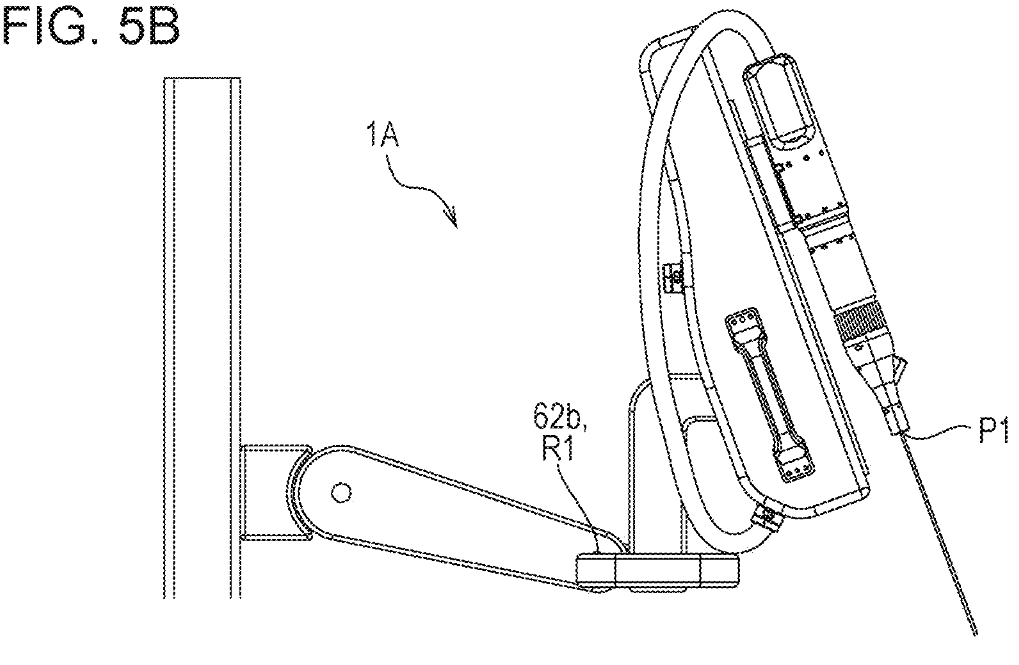
FIG. 5B is a schematic view of the medical system according to Example 1.
Figure 6:
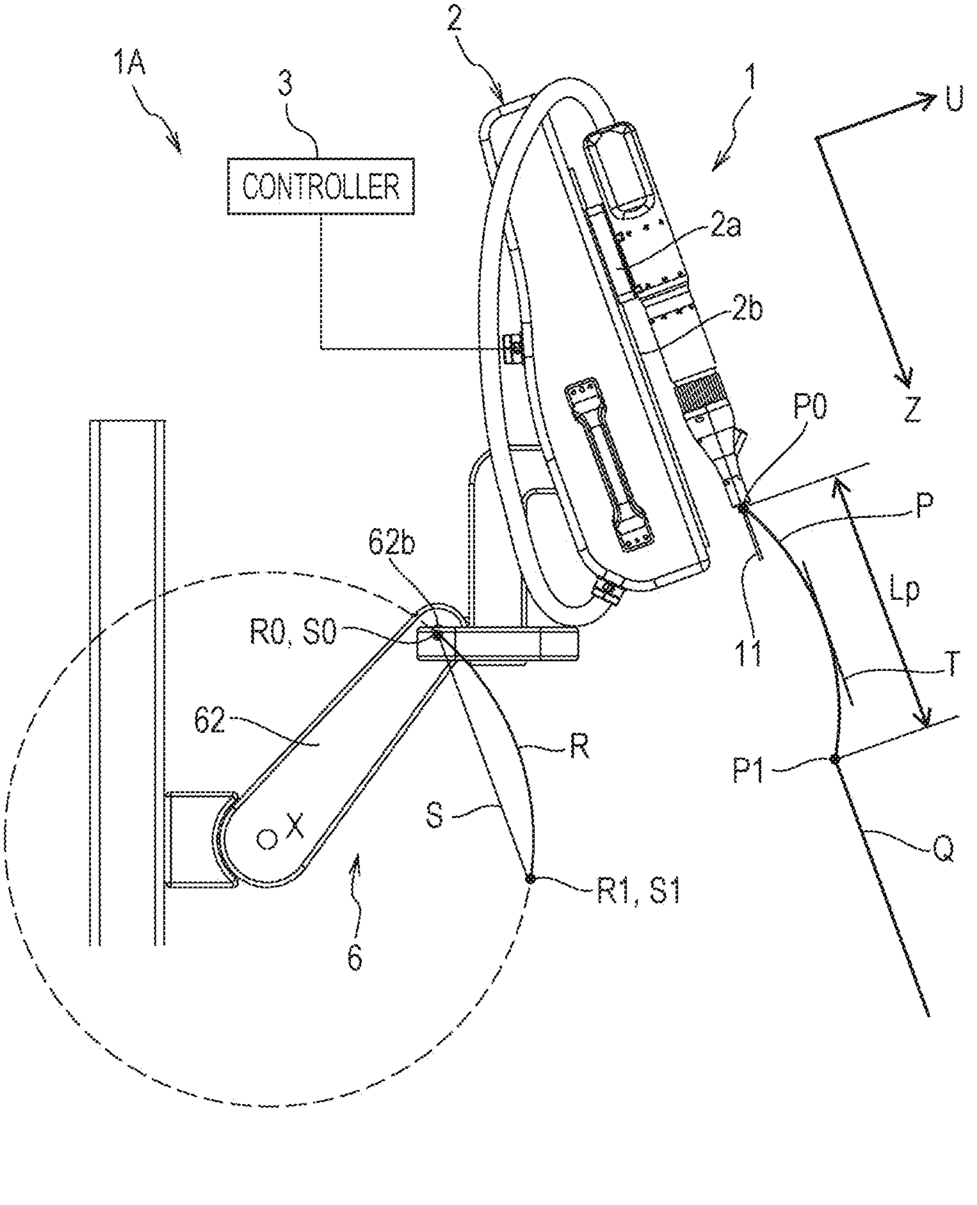
FIG. 6 is a diagram for describing an insertion track of the medical apparatus according to Example 1.

First, the manual insertion will be described with reference to FIG. 5A, FIG. 5B, and FIG. 6. FIG. 5A and FIG. 5B are each a schematic view of the medical system 1A according to Example 1. FIG. 6 is a diagram for describing an insertion track of the medical apparatus 1 according to Example 1.

First, as illustrated in FIG. 5A, the orientation and the position of the support base 2 are adjusted such that the catheter 11 is directed to an insertion portion (for example, an oral cavity, a nasal cavity, or the like of a patient) of a subject. The user adjusts the orientation of the support base 2 by turning the support base 2 in the W direction, in other words, around the axis V with respect to the supporting portion 63. In addition, the user adjusts the position of the support base 2 by, for example, moving the cart 7, turning the arm 6 about the axis X in the Y-direction, and adjusting (for example, adjusting the height of a bed, which is not illustrated, on which the patient is placed) the height of an insertion subject. The support 7*a* of the cart 7 may have an adjusting function of adjusting the height of the base portion 61 of the arm 6. In addition, an arm that has flexibility for positional adjustment may be further included between the base portion 61 and the support 7*a*. In FIG. 5A, the medical system 1A in a state in which the orientation and the position of the support base 2 have been adjusted is illustrated.

Next, the user grasps the handle 63*a* and turns the turning portion 62 of the arm 6 in the Y-direction, that is, around the axis X while pressing the unlocking button 63*a*1 to thereby integrally move the support base 2 mounted on the arm 6 and the medical apparatus 1. In FIG. 5B, a state of the medical system 1A after the manual insertion is illustrated.

Here, a track of the catheter 11 (proximal end) in the manual insertion is indicated by P in FIG. 6. A starting point P0 of the track P is a position before the manual insertion illustrated in FIG. 5A. An end point P1 of the track P is a position after the manual insertion illustrated in FIG. 5B. As illustrated in FIG. 6, the track P in the manual insertion has an arc shape and is identical (but the position thereof is moved) to a track R of the second joint shaft 62*b* of the arm 6 in the manual insertion. This is because, as described above, the orientation of each of the support base 2 and the medical apparatus 1 before and after the manual insertion is maintained substantially constant. In FIG. 6, the position of the second joint shaft 62*b* before the manual insertion is indicated by R0, and the position of the second joint shaft 62*b* after the manual insertion is indicated by R1. Therefore, the starting point P0 and the end point P1 of the track P correspond to R0 and R1 of the track R, respectively.

The track R is a track when the turning portion 62 of the arm 6 is turned about the axis X and thus moves on a plane perpendicular to the axis X. The track P moves on a plane parallel to the plane passing through the track R since the orientation of each of the support base 2 and the medical apparatus 1 before and after the manual insertion is maintained substantially constant. In other words, the track P also moves on a plane perpendicular to the axis X.

While, as described above, the orientation and the position of the support base 2 are adjusted such that the catheter 11 is directed to the insertion port of the subject before the manual insertion, the catheter 11 is preferably directed to the insertion portion of the subject even after the manual insertion. With the catheter 11 being directed to the insertion port of the subject even after the manual insertion, the need to readjust the position and the orientation of the catheter 11 is eliminated when the manual insertion is switched to the robot insertion. Therefore, when a direction perpendicular to the moving direction Z of the medical apparatus 1 moved by the moving stage 2*a* is indicated by U in FIG. 6, the movement amount (the movement amount of the track P in the U-direction) of the catheter 11 in the U-direction before and after the manual insertion is preferably small. Note that the catheter 11 does not move in the X-direction since the manual insertion is performed by turning of the turning portion 62 of the arm 6 around the axis X in the present example.

Here, a movement amount Lp of the catheter 11 in the Z-direction in the manual insertion is substantially determined by the structure of an insertion subject. Therefore, the position R0 of the second joint shaft 62*b* of the arm 6 and the orientation (Z-direction vector) of the support base 2 before the manual insertion may be preferably determined such that the movement amount of the catheter 11 in the U-direction is small when the catheter 11 is moved by the movement amount Lp in the Z-direction by the manual insertion.

For example, when the movement amount Lp of the catheter 11 in the Z-direction and the orientation (Z-direction vector) of the support base 2 are previously determined, the position R0 of the second joint shaft 62*b* of the arm 6 before the manual insertion can be determined as follows.

As illustrated in FIG. 6, a straight line S is drawn to be parallel to the Z-direction vector and to intersect the track R at two points and such that a straight-line distance between the two points is Lp. Here, when an intersection point of the track R and the straight line S on the upstream side in the Z-direction is referred to as S0 and another intersection point thereof on the downstream side in the Z-direction is referred to as S1, the position R0 of the second joint shaft 62*b* is determined to satisfy R0=S0 (and R1=S1). When the position R0 is determined in such a direction, the movement amount (the movement amount of the track P in the U-direction) of the catheter 11 in the U-direction before and after the manual insertion becomes 0 (zero).

Consequently, when the orientation and the position of the support base 2 are previously adjusted before the manual insertion such that the catheter 11 is directed to the insertion port of the subject, the catheter 11 is also directed to the insertion port of the subject even after the manual insertion.

Next, the robot insertion will be described in detail with reference to FIG. 6.

In the robot insertion, the catheter 11 moves in the Z-direction from a starting point at the position P1 after the manual insertion. Here, a track of the catheter 11 (proximal end) in the robot insertion is indicated by Q. As described above, the support base 2 is fixed to the supporting portion 63 such that the moving direction Z of the medical apparatus 1 moved by the moving stage 2*a* is perpendicular to the first joint shaft 62*a* (axis X) of the arm 6. Therefore, the track Q of the catheter 11 in the robot insertion moves on a plane perpendicular to the axis X.

The track P in the manual insertion and the track Q in the robot insertion both move on a plane perpendicular to the axis X, and the track P and the track Q are connected at the point P1. The track P and the track Q thus move on an identical plane perpendicular to the axis X.

After inserting the catheter 11 into the inside of the patient as the subject, the user performs work of observation, collection, resection, and the like of a lung tissue. After completed the work, the user extracts the catheter 11 from the inside of the patient as the subject. Extraction of the catheter is performed, for example, in the reverse order to the insertion thereof. That is, the moving stage 2*a* on which the medical apparatus 1 is mounted is moved in a direction of extraction from the inside of the patient by the motor, which is not illustrated, connected to the controller 3. Thereafter, the user extracts the catheter from the inside of the patient by manually moving the turning portion 62 of the arm 6 and thereby integrally moving the support base 2 mounted on the arm 6 and the medical apparatus 1.

As described above, according to the present example, the support base 2 supports the medical apparatus 1 to be movable along a plane perpendicular to the first joint shaft 62*a* (axis X). Therefore, when the user manually inserts the medical apparatus 1 into a lumen of the patient, the track P of the movement of the medical apparatus 1 by turning of the arm 6 and the track Q of the movement of the medical apparatus 1 by the robot insertion are on an identical plane perpendicular to the axis X of the arm 6 and are not shifted from each other. Thus, the manual insertion of the medical apparatus 1 can be performed in a state in which the medical apparatus 1 is attached to the support base 2, which eliminates the need for the user to perform operation and the like for attaching and detaching the medical apparatus 1. It is thus possible to improve operability of the medical apparatus 1.

In addition, according to the present example, it is possible to reduce the insertion length in the robot insertion by enabling the manual insertion by turning of the arm 6. Consequently, it is possible to shorten the movement stroke of the moving stage 2*a* and possible to downsize the support base 2. By downsizing the support base 2, it is possible to improve the operability of the medical apparatus 1.

While a method in which the position R0 of the second joint shaft 62*b* before the manual insertion is determined such that the movement amount of the catheter 11 in the U-direction before and after the manual insertion becomes 0 (zero) has be described in the present example, the method is a non-limiting example. Since the catheter 11 has a certain degree of flexibility, a sufficient effect can be obtained even if the movement amount in the U-direction is not 0. For example, it is sufficient that the starting point P0 and the end point P1 of the track P are aligned in the U-direction to a degree with which a tangent line T parallel to the Z-direction can be drawn at the track P. It is sufficient for the support base 2 to have a structure that can support the medical apparatus 1 such that the tangent line T that is parallel to a straight line along which the medical apparatus 1 moves is present with respect to the track of the medical apparatus 1 when the support base 2 is turned about the first joint shaft 62*a* via the arm 6.

In addition, according to the present example, the orientation of the support base 2 is maintained substantially constant, even when the support base 2 is turned about the axis X of the arm 6, due to the arm 6 being constituted by the four-joint link. When turned about the axis X, the arm 6 supports the support base 2 such that the orientation of the medical apparatus 1 is maintained substantially constant. Therefore, the orientation of the medical apparatus 1 supported by the support base 2 is also maintained substantially constant, and it is thus possible to perform the manual insertion easily. In addition, due to the arm 6 being constituted by the four-joint link, the support base 2 can be turned smoothly.

According to the present example, the arm 6 is provided with the lock mechanism, which is not illustrated, that locks the turning about the axis X. Therefore, the arm 6 can be prevented from moving unintentionally.

While a configuration in which the base portion 61 of the arm 6 is attached to the support 7*a* of the cart 7 has been described in the present example, an arm that has flexibility for positional adjustment may be further included, as described above, between the base portion 61 and the support 7*a*. When the arm is included between the base portion 61 and the support 7*a*, flexibility in positional adjustment of the support base 2 can be further improved.

In addition, while a configuration in which the axis X of the first joint shaft 62*a* is fixed with respect to the support 7*a* of the cart 7 has been described in the present example, it may be configured such that the angle of the axis X is adjustable to be inclined with respect to a floor surface. Further, the arm 6 may be directly attached to a wall surface or a ceiling.

While a case in which the catheter 11 is inserted by a procedure in which the robot insertion is performed after the manual insertion has been described in the present example, the case is a non-limiting example. For example, it may be configured such that the robot insertion is first performed and thereafter is switched to the manual insertion, and then, the robot insertion is performed again. In addition, extraction of the catheter 11 is not limited to be performed by the method performed in the reverse order to the insertion thereof and may be performed by a different procedure.

As described above, the medical apparatus 1 is attachable to and detachable from the support base 2, and connection between the medical apparatus 1 and the controller 3 is maintained even in a state (detached state) in which the medical apparatus 1 is detached from the support base 2. In another words, the controller 3 is electrically connected to the medical apparatus 1 constantly regardless of the attached/detached state of the medical apparatus 1 with respect to the support base 2. Such a configuration enables the user to manually insert and extract the catheter 11 into and from the inside of a patient in a state in which the medical apparatus 1 is held by the hand of the user. Therefore, manual insertion and extraction by turning of the arm 6 and manual insertion and extraction in a state in which the medical apparatus 1 is held by the hand of the user can be used in combination. For example, for insertion of the catheter 11, the catheter 11 can be advanced by the manual insertion by turning of the arm 6 and the robot insertion, and, for extraction of the catheter 11, the catheter 11 can be manually extracted in a state in which the medical apparatus 1 is held by the hand of the user. Consequently, flexibility for insertion and extraction of the catheter 11 is further improved.

Example 2

Figure 7:
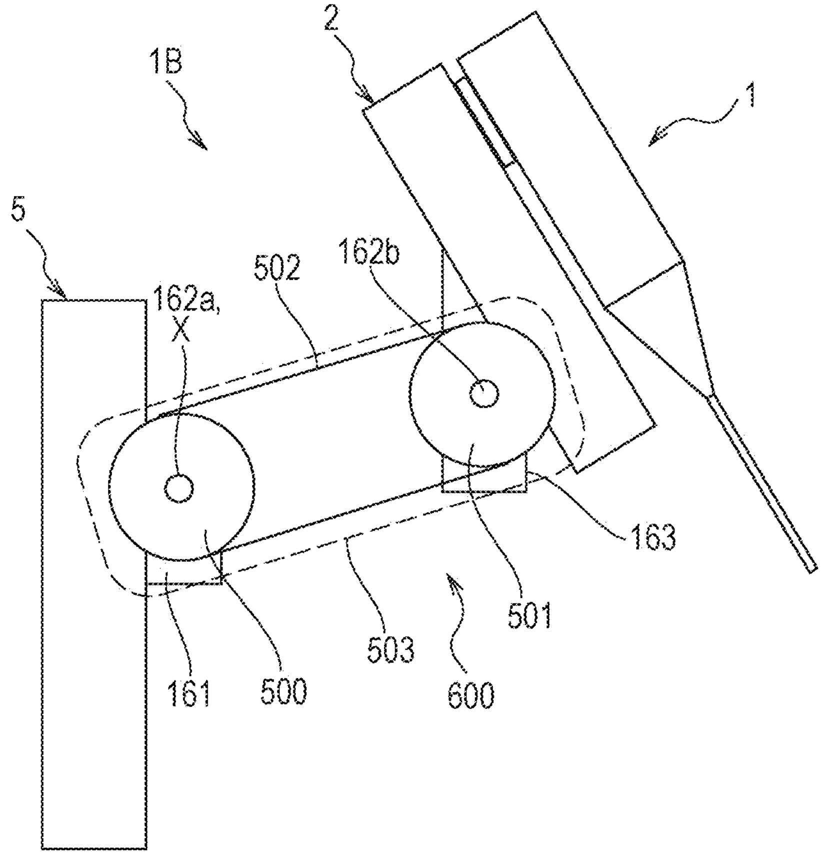
FIG. 7 is a diagram illustrating an internal structure of an arm according to Example 2.

With reference to FIG. 7, a medical system 1B according to Example 2 will be described. FIG. 7 is a diagram for describing an arm 600 of the medical system 1B. Note that components having reference signs common to those in Example 1 have configurations and effects that are substantially identical to those described in Example 1. Hereinafter, parts that differ from those in Example 1 will be described mainly.

In the present example, a configuration in which the orientation of the support base 2 is maintained substantially constant even when the support base 2 is turned about the axis X of the arm 600 will be described. FIG. 7 is a schematic view for describing an internal structure of the arm.

The arm 600 is constituted by a base portion 161, a link arm 503, and a supporting portion 163. The link arm 503 is indicated in FIG. 7 by a broken line so that the internal structure of the arm can be understood. The link arm 503 is provided with a first joint shaft 162*a* and a second joint shaft 162*b*. The link arm 503 is supported to be turnable with respect to each of the base portion 161 and the supporting portion 163. A pulley 500 as a first member and a pulley 501 as a second member are provided on the first joint shaft 162*a* and on the second joint shaft 162*b*, respectively. The pulley 500 and the pulley 501 have identical diameters.

The pulley 500 on the first joint shaft 162*a* is turnable with respect to the first joint shaft 162*a* of the link arm 503 and is fixed not to turn with respect to the base portion 161. The pulley 501 on the second joint shaft 162*b* is turnable with respect to the second joint shaft 162*b* of the link arm 503 and is fixed not to turn with respect to the supporting portion 163. An endless belt (belt) 502 as a third member is stretched over the pulley 500 and the pulley 501 so as not to slide relatively. The endless belt 502 has a function of maintaining the orientation of the pulley 501 to be substantially constant when the arm 600 is turned about the axis X of the first joint shaft 162*a*.

The user moves the support base 2 mounted on the arm 600 and the medical apparatus 1 integrally by turning the link arm 503 of the arm 600 around the axis X of the first joint shaft 162*a*. At this time, the pulley 501 turns (revolves) around the axis X while the endless belt 502 changes positions to contact the pulley 500 and the pulley 501 without sliding with respect to the pulley 500 and the pulley 501 in response to turning of the link arm 503. Here, since the pulley 501 is turnable with respect to the second joint shaft 162*b*, the pulley 501 and the second joint shaft 162*b* relatively turn when the pulley 501 turns (revolves) around the axis X, and the orientation of the pulley 501 is maintained substantially constant. With the orientation of the pulley 501 being maintained substantially constant, the orientation of the supporting portion 163 fixed to the pulley 501, the orientation of the support base 2 supporting the supporting portion 163, and the orientation of the medical apparatus 1 supporting the support base 2 are maintained substantially constant.

While a case in which the arm 600 includes the pulley 500, the pulley 501, and the endless belt 502 has been described in the present example, the case is a non-limiting example. For example, the pulley 500 and the pulley 501 may be replaced with sprockets having identical diameters, and the endless belt 502 may be replaced with an endless chain (chain).

Example 3

Figure 8:
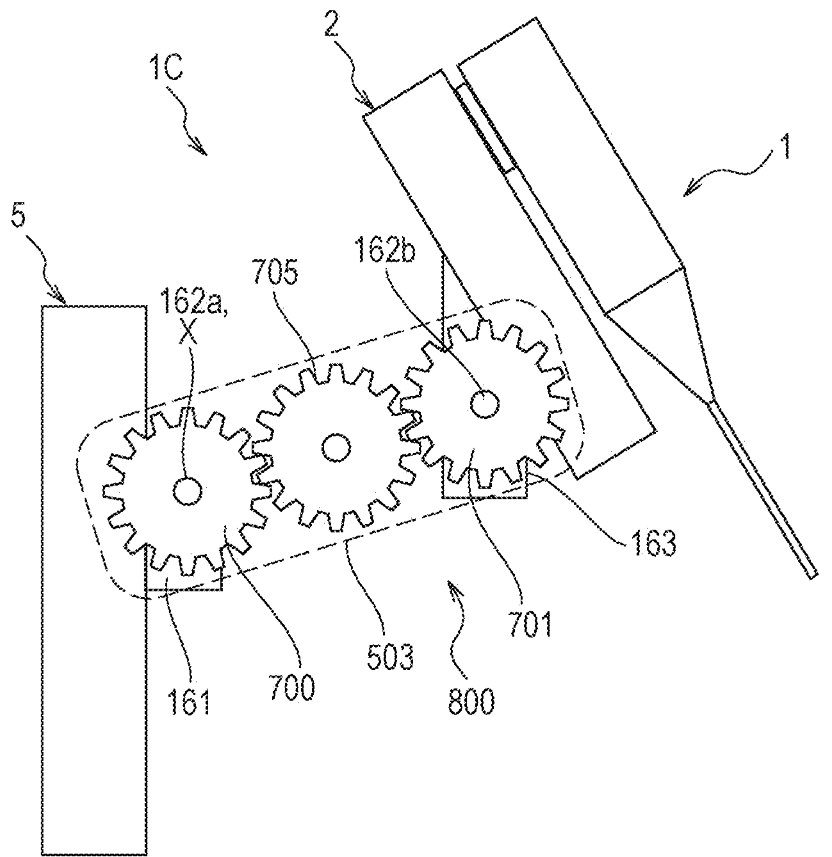
FIG. 8 is a diagram illustrating an internal structure of an arm according to Example 3.

With reference to FIG. 8, a medical system 1C according to Example 3 will be described. FIG. 8 is a diagram for describing an arm 800 of the medical system 1C. Note that components having reference signs common to those in Example 2 have configurations and effects that are substantially identical to those described in Example 2. Hereinafter, parts that differ from those in Example 2 will be described mainly.

The present example has a configuration in which the pulley 500 and the pulley 501 in Example 2 are replaced with a gear 700 and a gear 701 that have identical diameters, and an idler gear 705 is disposed between the gear 700 and the gear 701.

The gear 700 on the first joint shaft 162*a* is turnable with respect to the first joint shaft 162*a* of the link arm 503 and is fixed not to turn with respect to the base portion 161. The gear 701 on the second joint shaft 162*b* is turnable with respect to the second joint shaft 162*b* of the link arm 503 and is fixed not to turn with respect to the supporting portion 163. The gear 700 and the gear 701 each mesh with the idler gear 705. The idler gear 705 is supported between the first joint shaft 162*a* and the second joint shaft 162*b* to be turnable with respect to the link arm 503. The idler gear 705 has a function of maintaining the orientation of the gear 701 to be substantially constant when the arm 800 is turned about the axis X of the first joint shaft 162*a*.

The user moves the support base 2 mounted on the arm 800 and the medical apparatus 1 integrally by turning the link arm 503 of the arm 800 around the axis X of the first joint shaft 162*a*. At this time, in response to the turning of the link arm 503, the idler gear 705 turns (revolves) around the axis X while changing positions to mesh with the gear 700 and the gear 701. Here, since the gear 701 is turnable with respect to the second joint shaft 162*b*, the gear 701 and the second joint shaft 162*b* relatively turn when the idler gear 705 turns (revolves) around the axis X, and the orientation of the gear 701 is maintained substantially constant. With the orientation of the gear 701 being maintained substantially constant, the orientation of the supporting portion 163 fixed to the gear 701, the orientation of the support base 2 supporting the supporting portion 163, and the orientation of the medical apparatus 1 supporting the support base 2 are maintained substantially constant.

According to the present invention, operability of a continuum robot can be improved.

While the present invention has been described above with various examples, the present invention is not limited only to these examples and can be, for example, changed within the scope of the present invention. For example, part of the configuration described in each example may be combined with another example, and the modification described in an example may be applied to another example.

The present invention is not limited to the aforementioned embodiments and can be variously changed and modified without deviating from the spirit and the scope of the present invention. Accordingly, the following claims are attached to publicize the scope of the present invention. While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A continuum robot system comprising:

a continuum robot that includes a bendable body and a base portion at which the bendable body is provided;

a moving stage that supports the continuum robot such that the continuum robot is detachable from and attachable to the moving stage and is movable along a straight line;

a support base that supports the moving stage;

an arm that supports the support base and that is turnable about a first shaft;

a controller configured to control a movement of the moving stage and the continuum robot and be connected to both the continuum robot and the support base; and a cable configured to connect the continuum robot to the support base electrically, wherein the arm is configured to be operated manually by a user to move the support base and the continuum robot integrally, wherein the moving stage is configured to move with the continuum robot mounted on the moving stage along a plane perpendicular to the first shaft under a control of the controller, and wherein the cable electrically connects the controller to the continuum robot constantly regardless of an attached/detached state of the continuum robot with respect to the moving stage.

2. The continuum robot system according to claim 1, wherein the moving stage supports the continuum robot to be movable such that a tangent line parallel to the straight line is present with respect to a track of the continuum robot when the support base is turned about the first shaft via the arm.

3. The continuum robot system according to claim 1, wherein the arm supports the support base such that an orientation of the continuum robot is maintained substantially constant when the arm is turned about the first shaft.

4. The continuum robot system according to claim 3, wherein the arm is constituted by a four-joint link.

5. The continuum robot system according to claim 4, wherein the arm includes a supporting portion that supports the support base to be turnable, and wherein the four-joint link is connected to the supporting portion.

6. The continuum robot system according to claim 3, wherein the arm includes a first member that is provided at the first shaft;

a second member that is provided at a second shaft positioned opposite to the first shaft; and a third member that is in contact with each of the first member and the second member and that maintains an orientation of the second member to be substantially constant when the arm is turned about the first shaft.

7. The continuum robot system according to claim 6, wherein the arm includes a supporting portion that supports the support base to be turnable, and wherein the third member is fixed to the supporting portion.

8. The continuum robot system according to claim 6, wherein the first member and the second member are pulleys, and wherein the third member is a belt that is stretched over the pulleys.

9. The continuum robot system according to claim 6, wherein the first member and the second member are sprockets, and wherein the third member is a chain that is stretched over the sprockets.

10. The continuum robot system according to claim 6, wherein the first member and the second member are gears, and wherein the third member is an idler gear.

11. The continuum robot system according to claim 1, wherein the arm is provided with a lock portion that locks turning of the arm about the first shaft.

12. The continuum robot system according to claim 1, wherein the arm includes the first shaft and a second shaft, and wherein the arm supports the support base to be turnable about the second shaft.

13. The continuum robot system according to claim 1, comprising:

a cart that is movable, wherein the arm is supported by the cart.

14. The continuum robot system according to claim 1, wherein the continuum robot and the controller are connected wirelessly regardless of the attached/detached state of the continuum robot with respect to the moving stage.

15. A continuum robot system comprising:

a continuum robot that includes a bendable body and a base portion at which the bendable body is provided;

a moving stage that supports the continuum robot such that the continuum robot is detachable from and attachable to the moving stage and is movable along a straight line;

a support base that supports the moving stage;

an arm that supports the support base and that is turnable about a first shaft;

a controller configured to control a movement of the moving stage and the continuum robot and be connected to both the continuum robot and the support base; and a cable configured to connect the continuum robot to the support base electrically, wherein the arm is configured to be operated manually by a user to move the support base and the continuum robot integrally, wherein the moving stage is configured to move with the continuum robot mounted on the moving stage along a plane perpendicular to the first shaft under a control of the controller, wherein the controller is connected to the continuum robot constantly so that the controller controls the continuum robot regardless of an attached/detached state of the continuum robot with respect to the moving stage, and wherein the controller controls the continuum robot via the cable regardless of the attached/detached state of the continuum robot with respect to the moving stage.

* * * * *